United States Patent [19]
Maiese et al.

[11] Patent Number: 5,939,267
[45] Date of Patent: Aug. 17, 1999

[54] METHODS FOR THE TEMPORAL ANALYSIS OF PROGRAMMED CELL DEATH IN LIVING CELLS

[75] Inventors: Kenneth Maiese, Birmingham; Andrea M. Vincent, Detroit, both of Mich.

[73] Assignee: Wayne State University, Detroit, Mich.

[21] Appl. No.: 09/144,045

[22] Filed: Aug. 31, 1998

[51] Int. Cl.$^6$ .................................................. C12Q 1/68
[52] U.S. Cl. ................................................ 435/6; 435/29
[58] Field of Search ............................................ 435/6, 29

[56] References Cited

U.S. PATENT DOCUMENTS

| | | | |
|---|---|---|---|
| 5,766,626 | 6/1998 | Gross | 424/450 |
| 5,834,196 | 11/1998 | Reutelingsperger | 435/6 |

OTHER PUBLICATIONS

Alison, M.R. et al., "Apoptosis: a gene–directed programme of cell death," *J RCP* 26(1):25–35 (1992).

Allen, R.T. et al., "Morphological and Biochemical Characterization and Analysis of Apoptosis," *J. Pharmacol Toxicol. Methods* 37:215–228 (1997).

Andree, H.A. et al., "Binding of Vascular Antigoagulant α (VACα) to Planar Phospholipid Bilayers," *J. Biol. Chem.* 265(9):4923–4928 (1990).

Bratton, D.L. et al., "Appearance of Phosphatidylserine on Apoptotic Cells Requires Calcium–mediated Nonspecific Flip–Flop and Is Enhanced by Loss of the Aminophospholipid Translocase," *J. Biol. Chem.* 272(42):26159–26165 (1997).

Deckwerth, T.L. et al., "Temporal Analysis of Events Associated with Programmed Cell Death (Apoptosis) of Sympathetic Neurons Deprived of Nerve Growth Factor," *J. Cell Biol.* 123(5):1207–1222 (1993).

Didier, M. et al., "DNA Strand Breaks Induced by Sustained Glutamate Excitotoxicity in Primary Neuronal Cultures," *J. Neurosci.* 16(7):2238–2250 (1996).

Gurtu, V. et al., "Detection Of Early–Stage Apoptosis In Three Adherent Mammalian Cell Lines Using The ApoAlert™ Annexin V Apoptosis Kit," www.clontech.com/archive/Jan97UPD/ApoAlertarticle.html (Jul. 2, 1997).

Hara, A. et al., "DNA fragmentation in granular cells of human cerebellum following global ischemia," *Brain Res.* 697:247–250 (1995).

Hill, I.E. et al., "DNA fragmentation indicative of apoptosis following unilateral cerebral hypoxia–ischemia in the neonatal rat," *Brain Res.* 676:398–403.

Homburg, C.H. et al., "Human Neutrophils Lose Their Surface FctRIII and Acquire Annexin V Binding Sites During Apoptosis In Vitro," *Blood* 85(2):532–540 (1995).

Kerr, J.F. et al., "Apoptosis: A Basic Biological Phenomenon With Wide–Ranging Implications In Tissue Kinetics," *Brit. J. Cancer* 26:239–257 (1972).

Koopman, G. et al., "Annexin V for Flow Cytometric Detection of Phosphatidylserine Expression on B Cells Undergoing Apoptosis," *Blood* 84(5):1415–1420 (1994).

Lo, A.C. et al., "Apoptosis in the Nervous System: Morphological Features, Methods, Pathology, and Prevention," *Arch. Histol. Cytol.* 58(2):139–149 (1995).

Maiese, K. et al., "Neuroprotection by Peptide Growth Factors Against Anoxia and Nitric Oxide Toxicity Requires Modulation of Protein Kinase C," *J. Cereb Blood Flow Metab.* 15:440–449.

Maiese, K. et al., "Peptide Growth Factors Protect against Ischemia in Culture by Preventing Nitric Oxide Toxicity," *J. Neurosci.* 13(7):3034–3040 (1993).

Maiese, K. et al., "Protein Kinases Modulate the Sensitivity of Hippocampal Neurons to Nitric Oxide Toxicity and Anoxia," *J. Neurosci. Res.* 36:77–87 (1993).

Maiese, K., "From the Bench to the Bedside: The Molecular Management of Cerebral Ischemia," *Clinical Neuropharm.* 21:1–7 (1998).

Maiese, K. et al., "Neuroprotection of Lubeluzole Is Mediated Through the Signal Transduction Pathways of Nitric Oxide," *J. Neurochem.* 68(2):710–714 (1997).

Maiese, K. et al., "Nitric oxide: a downstream mediator of calcium toxicity in the ischemic cascase," *Neurosci. Lett.* 166:43–47 (1994).

Maiese, K., "Cellular Mechanisms of Neuronal Protection by Metabolic Glutamate Receptors," Robertson JT, Nowak TS (eds). Armonk, NY: Futura Publishing Company, Inc. 281–297 (1998).

Maiese, K. et al., "Cellular Mechanisms of Protection by Metabotropic Glutamate Receptors During Anoxia and Nitric Oxide Toxicity," *J. Neurochem.* 66:2419–2428 (1996).

Martin, S.J. et al., "Early Redistribution of Plasma Membrane Phosphatidylserine Is a General Feature of Apoptosis Regardless of the Initiating Stimulus: Inhibition by Overexpression of Bcl–2 and Abl," *J. Exp. Med.* 182:1545–1556 (1995).

(List continued on next page.)

*Primary Examiner*—James Ketter
*Attorney, Agent, or Firm*—Harness, Dickey & Pierce, P.L.C.

[57] ABSTRACT

Methods for determining the induction and assessing the course of programmed cell death (PCD) over time in living cells are provided. The methods of the present invention comprise the steps of maintaining a viable cell on a slide, staining the cell with annexin V to label any phosphatidylserine residues which may be present on the cell surface, visualizing the stained cell, removing the stain, sustaining the cell in culture, restaining the cell with annexin V to again label any phosphatidylserine residues present on the cell surface and visualizing the stained cell. The methods of the present invention are performed with cells maintained in a viable state, thereby allowing detection of the induction and assessment of the progression of PCD over time.

15 Claims, 6 Drawing Sheets

OTHER PUBLICATIONS

Palluy, O. et al., "Nitric oxide induces cultured cortical neuron apoptosis," *Neuroscience Letters* 208:1–4 (1996).

Rimon, G. et al., "Increased Surface Phosphatidylserine Is an Early Marker of Neuronal Apoptosis," *J. Neurosci. Res.* 48:563–570 (1997).

Tait, J.F. et al., "Phospholipid Binding of Annexin V: Effects of Calcium and Membrane Phosphatidylserine Content," *Arch Biochem Biophys* 298(1):187–191 (1992).

Takei, N. et al., "Neutrotrophic effects of annexin V on cultured neurons from embryonic rat brain," *Neurosci Lett.* 171:59–62 (1994).

Vanags, D.M. et al., "Protease Involvement in Fodrin Cleavage and Phosphatidylserine Exposure in Apoptosis," *J. Biol. Chem.* 271(49):31075–31085 (1996).

van Engeland, M. et al., "A Novel Assay to Measure Loss of Plasma Membrane Asymmetry During Apoptosis of Adherent Cells in Culture," *Cytometry* 24:131–139 (1996).

van Engeland, M. et al., "Annexin V–Affinity Assay: A Review on an Apoptosis Detection System Based on Phosphatidylserine Exposure," *Cytometry* 31:1–9 (1998).

Vincent, A.M. et al., "Metabotropic Glutamate Receptors Prevent Nitric Oxide–Induced Programmed Cell Death," *J. Neurosci. Res.* 50:549–564 (1997).

Wyllie, A.H. et al., "Cell Death: The Significance of Apoptosis," *Int. Rev. Cytology* 68:251–306 (1980).

Zhang, G. et al., "Early Detection of Apoptosis Using a Fluorescent Conjugate of Annexin V," *Bio Techniques* 23(3):525–531 (1997).

METHODS FOR THE TEMPORAL ANALYSIS OF PROGRAMMED CELL DEATH IN LIVING CELLS

SPONSORSHIP

Work on this invention was sponsored in part by the National Institutes of Health Grant No. K08-NJ-01599. The Government may have certain rights in the invention.

FIELD OF THE INVENTION

The present invention relates generally to methods for temporally analyzing programmed cell death in living cells and more particularly, to methods for determining the induction and assessing the course of programmed cell death over time.

BACKGROUND OF THE INVENTION

Programmed cell death (PCD) is a selective genetically controlled process of cell deletion. This contrasts with cellular necrosis, a passive cellular injury that results in loss of membrane integrity and cell lysis. Wyllie, A. H. et al., *Int. Rev. Cytology* 68:251–306 (1980). A cell in PCD can be identified by nuclear chromatin condensation, nuclear shrinkage, ordered cleavage of the nuclear DNA, compactness of cytoplasmic organelles, and the appearance of an irregular plasma membrane. Kerr, J. F. et al., *Brit. J. Cancer* 26:2392–57 (1972). A discrete change which occurs early, before nuclear alterations, is the redistribution of phosphatidylserine from the plasma membrane inner leaflet to become exposed at the cell surface. The execution of PCD is essential in the control of tissue shape and size (Alison, M. R. et al., *J RCP* 26:25–35 (1992)) and thus plays an important role during development of the nervous system. Deckwerth, T. L. et al., *J. Cell Biol.* 123:1207–1222 (1993).

PCD is a necessary component not only in the development of the nervous system (Lo, A. C. et al., *Arch. Histol. Cytol.* 58:139–139 (1995)), but also in the pathophysiological conditions that lead to neurodegeneration. Neuronal PCD can be induced by a variety of toxic insults to the nervous system, such as cerebral ischemia (Hara, A. et al., *Brain Res.* 697:247–250 (1995)), excitotoxicity (Didier, M. et al., *J. Neurosci.* 16:2238–2250 (1996)), and nitric oxide (NO) exposure (Maiese, K., *Clinical Neuropharm.* 21:1–7 (1998); Palluy, O. et al., *Neuroscience Letters* 208:1–4 (1996); Vincent, A. M. et al., *Exp. Cell. Res.* in press (1998)). In some experimental systems, free radical NO induced PCD induction is both rapid and robust occurring within hours in at least 70% of the neuronal population. Vincent, A. M. et al., *J. Neurosci. Res.* 50:549–564 (1997). As a result of its ability to modulate neuronal survival, NO has become aggressively employed as a valuable tool to dissect the downstream cellular pathways that mediate PCD. Maiese, K. et al., *J. Neurochem.* 68:710–714 (1997); Maiese, K., *Clinical Neuropharm.* 21:1–7 (1998); Maiese, K. et al., *Neurosci. Lett.* 166:43–47 (1994); Vincent, A. M. et al., *J. Neurosci. Res.* 50:549–564 (1997).

The externalization of phosphatidylserine is known to occur very early during PCD. This phenomenon was first described in lymphocytes (Koopman, G. et al., *Blood* 84:1415–1420 (1994)), but has since been attributed to many murine and human cell types (Martin, S. J. et al., *J. Exp. Med.* 182:1545–1556 (1995)). A recent report has demonstrated that increased surface phosphatidylserine is an early marker of PCD in neuronal cell lines. Rimon, G. et al., *J. Neurosci. Res.* 48:563–570 (1997). Membrane asymmetry is believed to be maintained through the activity of aminophospholipid translocase. Vanags, D. M. et al., *J. Biol. Chem.* 271: 31075–31085 (1996). Phosphatidylserine externalization during PCD could result from reversal of aminophospholipid translocase activity, or loss of this enzyme coupled with random externalization of membrane phospholipids. Bratton, D. L. et al., *J. Biol. Chem.* 272:26159–26165 (1997). The presence of an unidentified "inside-outside phosphatidylserine translocase" also has been proposed. Allen, R. T. et al., *J. Pharmacol Toxicol Methods* 37:215–228 (1997). Factors known to inhibit PCD, such as trophic factors (Maiese, K. et al., *J. Cereb Blood Flow Metab.* 15:440–449 (1995); Maiese, K. et al., *J. Neurosci.* 13:3034–3040 (1993)), metabotropic glutamate receptor activation (Maiese, K., Robertson JT, Nowak TS (eds). Armonk, NY: Futura Publishing Company, Inc. 281–297 (1998); Maiese, K. et al., *J. Neurochem.* 66:2419–2428 (1996); Vincent, A. M. et al., *J. Neurosci. Res.* 50:549–564 (1997); Vincent, A. M. et al., Exp. Cell Res. in press (1998)), or benzothiazole administration (Maiese, K. et al., *J. Neurochem.* 68:710–714 (1997)), also can prevent phosphatidylserine exposure, suggesting that this event may be an integral part of the PCD pathway which occurs only after the cell has committed to die.

Since the majority of neuronal injury can occur through the induction of PCD, the ability to rapidly identify the onset and progression of PCD has become crucial to elucidate the multiple molecular mechanisms that modulate PCD. Current studies that characterize PCD rely on a variety of "fixed" assays to identify the end stages of PCD that include gel electrophoresis DNA fragmentation assays, DNA 3'-OH end labeling, electron microscopy, and hematoxylin and eosin staining. Hill, I.E. et al., *Brain Res.* 676:398–403 (1995); Maiese, K., *Clinical Neuropharm.* 21:1–7 (1998); Vincent, A. M. et al., *J. Neurosci Res.* 50:549–564 (1997). A recent study defined PCD sequentially in hippocampal neuronal cultures, using techniques which do not permit the later reassessment of the neuronal population. Maiese, K., *J. Neurochem.* 68:710–714 (1997); Vincent, A. M. et al., *Exp. Neurol.* (in press) (1998); Vincent, A. M. et al., *J. Neurosci Res.* 50:549–564 (1997); Vincent, A. M. et al., *Exp. Cell Res.* (in press) (1998). Other assays have incorporated the use of annexin V, a member of a family of calcium-dependent phospholipid-binding proteins, that possesses strong affinity for phosphatidylserine. Andree, H. A. et al., *J. Biol. Chem.* 265:4923–4928 (1990). Since phosphatidylserine translocation occurs early in PCD when cell membrane integrity is still intact, flow cytometric analysis using fluorescein isothiocyanate- labeled annexin V is now widely used as a quantitative measure of early PCD. Homburg, C. H. et al., *Blood* 85:532–540 (1995); Koopman, G. et al., *Blood* 84:1415–1420 (1994); Vanags, D. M. et al., *J. Biol. Chem.* 271:31075–31085 (1996). Yet, flow cytometric techniques have limited application to adherent cultures, since harvesting of the sample generates certain mechanical membrane damage, and the use of trypsin can artificially induce phosphatidylserine exposure. van Engeland, M. et al., *Cytometry* 24:131–139 (1996). Assays that eliminate cell harvesting continue to require cell fixation, i.e., non-viable cells. Rimon, G. et al., *J. Neurosci. Res.* 48:563–570 (1997).

It would thus be desirable to provide a method for analyzing PCD in living cells with minimal disruption of the cells. It would also be desirable to provide a method for temporally analyzing PCD in living cells wherein the onset and subsequent progression of PCD may be observed.

SUMMARY OF THE INVENTION

Methods for determining the induction and assessing the course of programmed cell death (PCD) over time in living cells are provided. The methods of the present invention comprise the steps of maintaining a viable cell on a slide, staining the cell with annexin V to label any phosphatidylserine residues which may be present on the cell surface, visualizing the stained cell, removing the stain, restaining the cell with annexin V to again label any phosphatidylserine residues present on the cell surface and visualizing the stained cell. The methods of the present invention are performed with cells maintained in a viable state, thereby allowing detection of the induction and assessment of the progression of PCD over time.

Additional objects, advantages, and features of the present invention will become apparent from the following description and appended claims, taken in conjunction with the accompanying drawings.

BRIEF DESCRIPTION OF THE DRAWINGS

The various advantages of the present invention will become apparent to one skilled in the art by reading the following specification and subjoined claims and by referencing the following drawings in which:

DETAILED DESCRIPTION OF THE PREFERRED EMBODIMENTS

Figures 1A, 1B:
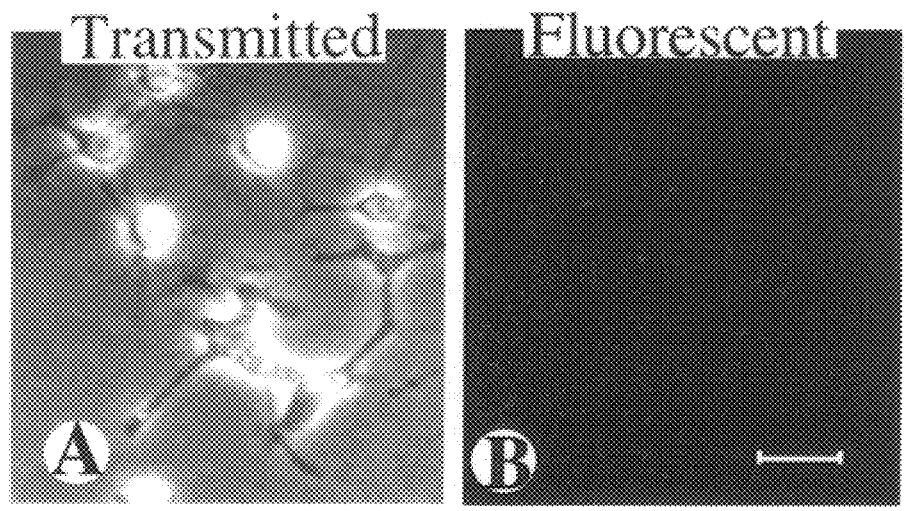
FIGS. 1A–1H are a series of photomicrographs of the same microscopic field over time, illustrating PCD following free radical injury may be identified by reversible annexin V labeling.

Methods for analyzing the induction and course of programmed cell death (PCD) over time in living cells are provided. In one embodiment, the method of the present invention comprises the steps of staining a viable cell with annexin V to label phosphatidylserine residues which may be present on the cell surface, visualizing the stained cell, removing the annexin V, sustaining the cell in culture, restaining the cell with annexin V, and again visualizing the cell for phosphatidylserine residues. In the methods of the present invention, cells are maintained in a viable state so that the course of PCD progression over time may be observed. Thus, by employing the reversible calcium dependent nature of annexin V-binding to phosphatidylserine (Tait, J. F. et al., *Arch Biochem Biophys* 298:187–191 (1992)), methods for the continuous assessment of the initiation and progression of PCD over time in living cells are provided.

The methods of the present invention thus offer a unique approach to investigating the earliest stages of PCD, as well as the progression of PCD, in viable cells. Various applications of the methods of the present invention will be appreciated by those skilled in the art and include, without limitation, the detection of disease states (e.g., neurodegeneration, cancer, infection, etc.), the investigation of therapeutic modalities against disease states involving PCD, and the assessment of possible toxins and injury states.

Thus, in one embodiment, the method of the present invention comprises maintaining a cell in a viable state while performing the steps of: a) staining the cell with annexin V, b) visualizing the stained cell, c) removing the annexin V, d) contacting the cell with a therapeutic agent, e) restaining the cell with annexin V, and f) visualizing the cell. By maintaining the cell in a viable state, the effect of the therapeutic agent on PCD may be assessed by observing whether the therapeutic agent caused a change (i.e., increase of decrease) in the presence of phosphatidylserine residues on the cell surface. It will be appreciated that any therapeutic agent may be employed in the methods of the present invention, including but not limited to, those known to increase or decrease PCD, such as metabotropic glutamate receptors, benzothiazole and peptide growth factors. It will also be appreciated that more than one therapeutic agent may be introduced, simultaneously or sequentially. Moreover, the effect of both intracellular and extracellular acting agents may be analyzed by the provided methods. It will further be appreciated that the step of contacting the cell with a therapeutic agent may be performed before or after the cell has been exposed to a known PCD causing agent, or simultaneously therewith.

In another embodiment, the method of the present invention comprises maintaining a cell under conditions known to keep the cell in a viable state while performing the steps of: a) staining the cell with annexin V, b) visualizing the stained cell, c) removing the annexin V, d) contacting the cell with an agent which is known to be a toxin or is suspected of having toxic characteristics, e) restaining the cell with annexin V, and f) visualizing the cell. By maintaining the cell under conditions known to keep the cell in a viable state, the effect of the agent on PCD may be assessed by observing whether the agent caused a change in the presence of phosphatidylserine residues on the cell surface. Any agent may be employed in the method including, without limitation, known PCD-causing agents such as nitric oxide (NO), glutamate and environmental toxins such as manganese.

In yet another embodiment, the effect of various environmental states on PCD may be analyzed by the methods of the present invention. For example, the methods of the present invention may be performed in an environment with little or no oxygen by performing the method in an anoxic chamber, such as a sealed container. The effect of other environmentally stressful conditions (e.g., high or low atmosphere, high or low heat, etc.) on PCD may also be analyzed by performing the method in a chamber replicating the stressful condition.

It will be appreciated that more than one variable may be employed and analyzed in the methods of the present invention. For example, a cell may be simultaneously or sequentially exposed to a known toxic agent and a therapeutic agent. Likewise, a cell may be exposed to a therapeutic agent under environmentally stressful conditions. It will further be appreciated that while the methods of the present invention are described as including one re-staining and re-visualizing of a cell, numerous re-staining and re-visualization steps may be performed.

In performing the methods of the present invention, cells are stained with annexin V by exposing the cells to a binding buffer containing calcium. The binding buffer is an isoosmotic buffered solution that maintains the cells in a physiologically viable state and preferably comprises $CaCl_2$ and annexin V. The binding buffer is preferably warm, e.g., at a temperature of about 37° C. The annexin V is removed from the cells by exposing the cells to a calcium-free dissociation buffer. The dissociation buffer is also an isoosmotic buffered solution that maintains the cells in a physiologically viable state and preferably comprises $MgCl_2$. The dissociation buffer is also preferably at a temperature of about 37° C.

As used herein, the term "visualize" is meant to include visualization via microscopy, e.g., visible light microscopy and fluorescence.

In order to more fully demonstrate the advantages arising from the present invention, the following Specific Example is set forth. It is to be understood that the following is by way of example only and is not intended as a limitation on the scope of the invention, e.g., although the analysis of neuronal cells is described, it will be appreciated that any adherent cell type may be employed in the methods of the present invention, e.g., endothelial, cells, fibroblasts, epithelial cells and stromal cells. Normally non-adherent cells, e.g., thymocytes, that are immobilized may also be employed. With respect to those cell types that are known to bind annexin naturally, any naturally-bound annexin present on the cell surface may first be removed by washing in appropriate solution or, the amount of natural staining may be used as the baseline with increases or decreases, an indication of increased or decreased phosphatidylserine residues on the cell surface. Thus, the present invention may be employed to analyze PCD in any cell type.

SPECIFIC EXAMPLE

Materials and Methods

Primary hippocampal neuronal cultures. The hippocampi were obtained from 1-day-old Sprague-Dawley rat pups following institutional guidelines and incubated in dissociation medium (90 mM $Na_2SO_4$, 30 mM $K_2SO_4$, 5.8 mM $MgCl_2$, 0.25 mM $CaCl_2$, 10 mM kynurenic acid, and 1 mM HEPES with the pH adjusted to 7.4) containing papain (10 U/ml) and cysteine (3 mmol/L) for two 20-min periods. The hippocampi were then rinsed in dissociation medium and incubated in dissociation medium containing trypsin inhibitor (10–20 U/ml) for three 5 minute periods. The neurons were washed in growth medium (Leibovitz's L-15 medium, GibcoBRL, Gaithersburg, Md.) containing 6% sterile rat serum (Bioproducts for Science, Indianapolis, Ind.), 150 mM $NaHCO_3$, 2.25 mg/ml of transferrin, 2.5 $\mu$g/ml of insulin, 10 nM progesterone, 90 $\mu$M putrescine, 15 nM selenium, 35 mM glucose, 1 mM L-glutamine, penicillin and streptomycin (50 $\mu$g/ml), and vitamins. The dissociated neurons were plated at a density of ~$1.5 \times 10^6$ cells/mm$^2$ in 35 mm polylysine/laminin-coated plates (Falcon Labware, Lincoln Park, N.J.). Neurons were maintained in growth medium at 37° C. in a humidified atmosphere of 5% $CO_2$ and 95% room air. All experiments were performed with neurons that had been in culture for 2 weeks. Non-neuronal cells accounted for 10–20% of the total cell population.

Experimental treatments. NO administration was performed by replacing the culture media with media containing either sodium nitroprusside (SNP, 300 $\mu$M) (Sigma, St Louis, Mo.) or 6-(2-hydroxy-1-methyl-2-nitrosohydrazino)-N-methyl-1-hexanamine (NOC-9, 300 $\mu$M) (Calbiochem, San Diego, Calif.) for 5 minutes. It was previously demonstrated that each of these agents yields neuronal injury through a mechanism that involves the direct release of NO with a 5 minute application of 300 $\mu$M resulting in the death of approximately 70–80% of neurons over a 24 hour period. Maiese, K. et al., *J. Neurosci.* 13:3034–3040 (1993); Maiese, K. et al., *J. Neurosci. Res.* 36:77–87 (1993). More than one NO generator is used as a control to demonstrate that the neurons were responding to NO rather than to other by-products of these agents. Following treatment with the NO donors, the culture medium was replaced with fresh growth medium and the cultures were placed in a normoxic, humidified incubator at 37° C. with 5% $CO_2$ for periods determined by the specific experimental paradigm.

Staining for externalization of phosphatidylserine residues. Annexin V conjugated to phycoerythrin (PE) was purchased from R&D Systems (Minneapolis, Minn., see package insert, Annexin V-Phycoerythrin, Catalog Number: NXPE, 100 Tests, expressly incorporated by reference). The stock solution was 30 $\mu$g/mL concentration. This was diluted directly before use 1:10 in warmed (37° C.) binding buffer (10 mM HEPES, pH 7.5, 150 mM NaCl, 5 mM KCl, 1 mM $MgCl_2$, 1.8 mM $CaCl_2$). The growth medium was removed from culture plates, annexin V conjugate was applied in a final concentration of 3 $\mu$g/mL, and then incubated at 37° C. in a humidified atmosphere in the dark for 10 minutes. Plates were then rinsed twice using fresh binding buffer, and neurons were examined using Leitz DMIRB microscope (Leica, McHenry, Ill.) and Oncor Image 2.0 imaging software (Oncor, Inc., Gaithersburg, Md.). Images were acquired using a cooled charge-coupled device with both transmitted light, as well as fluorescent single excitation light at 490 nm and detected emission at 585 nm.

Following examination, the annexin V label was detached by washing three times in dissociation buffer (10 mM HEPES, pH 7.5, 150 mM NaCl, 5 mM KCl, 2.8 mM $MgCl_2$) which differed from binding buffer in that the calcium was replaced with magnesium. Plates could then be re-examined to confirm that the annexin V was completely removed, then returned to the incubator for a further specified period. Plates could then be re-stained using the same method. By drawing a grid on the bottom of the culture dish (or similar marking system), the same fields of neurons could be re-located for sequential imaging. Access to a mechanically controlled microscope stage further enables the re-assessment of individual cells.

To maintain cell adherence to the culture plates, extreme care was required during dissociation of the label since cell-to-cell and cell-to-matrix adhesion processes are calcium-dependent. The magnesium ions that replace the calcium in the dissociation buffer assist in maintaining cell adherence to the culture surface. Removal of annexin V in calcium-free conditions also was performed gently with minimal shear forces at the culture surface. A longer incubation in a calcium-free buffer or undue agitation of the neuronal layer may result in detachment of the neurons and was thus avoided.

Neuronal survival assays. Hippocampal neuronal injury was determined by bright field microscopy using a 0.4% trypan blue dye exclusion method 24h following treatment with the NO donors. Neurons were identified by morphology. The mean survival was determined by counting 9 randomly selected non-overlapping fields with each containing approximately 10–20 neurons (viable+non-viable) in each 35 mm Petri dish. The mean survival from each culture dish represents an n=1 determination.

Transmission electron microscopy of hippocampal neurons. Electron microscopy was used to provide visualization of the neuronal subcellular structure to assess changes in the cell nucleus at times relevant to the externalization of phosphatidylserine. Neurons were grown on 35 mm glass coverslips coated with laminin and poly-L-lysine. Following treatments as indicated, the hippocampal neurons were fixed at 4° C. for 1.5 hours with a fixative consisting of 1:1:1 of 2% aqueous $OSO_4$, 2.5% glutaraldehyde in 0.1M phosphate buffer (pH 7.4) and 0.2M phosphate buffer (pH 7.4). Neurons were then rinsed with phosphate buffer and dehydrated with graded ethanol in the following sequence: 50% for 5 min, 70% for 10 min, 85% for 10 min, 95% for 10 min, 100% for 10 min, and an additional 30 min in 100% ethanol. Neurons were removed from the coverslips and placed into a glass scintillation vial containing propylene oxide (PO). Dehydration was performed with three changes of PO, each for 10 min and one change for 30 min. Neurons were infiltrated with mixture of 1:1 Epon-Araldite and PO for 1 hour, with 3:1 mixture for 3 hour, with straight Epon-Araldite for 1–4 days, and then with Epon-Araldite added accelerator for 24–48 hours. Neurons were embedded in fresh Epon-Araldite, and ultrathin sections were mounted on copper grids and stained with 3% aqueous uranyl acetate and Reynolds' lead citrate. These were viewed using a JEM 1010 transmission electron microscope (Jeol, Japan).

Statistical analysis. For each experiment, the mean and standard error were determined. The sample size is defined in each individual experiment. Statistical significance was assessed using the Student's paired t test and ANOVA with 95% confidence intervals.

Results

Figures 1C, 1D:
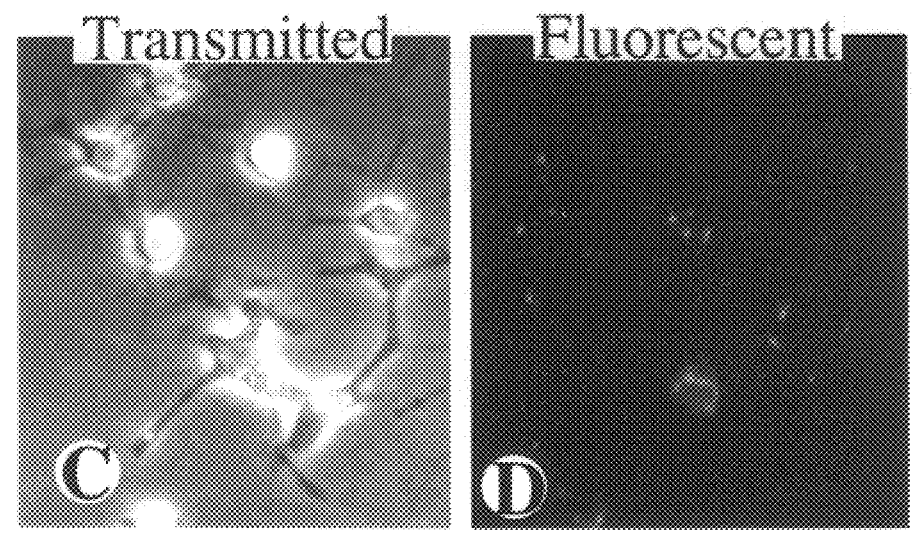
Figure 1E:
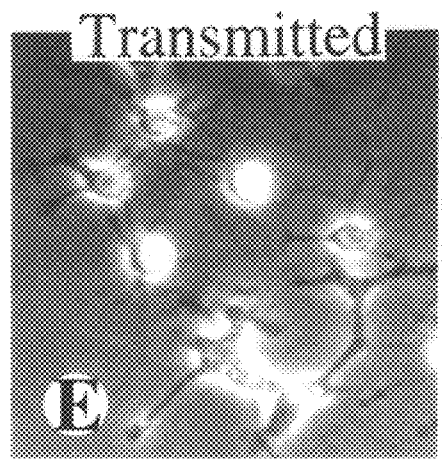
Figure 1F:
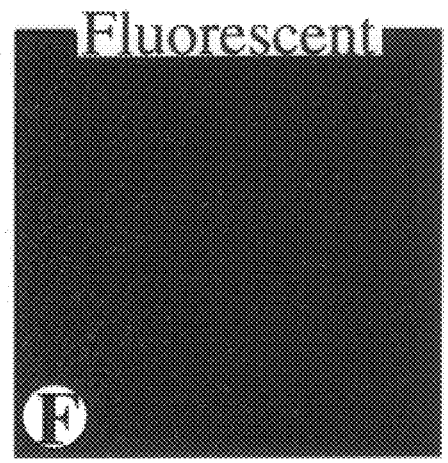
Figure 1G:
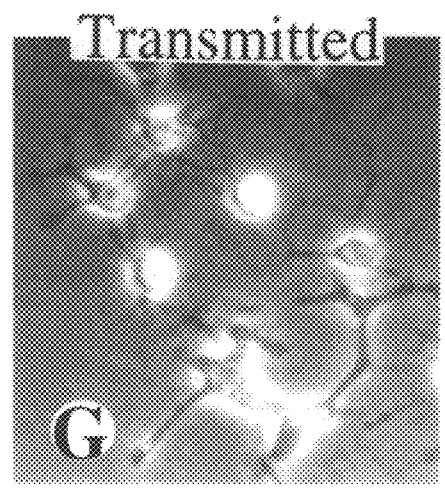
Figure 1H:
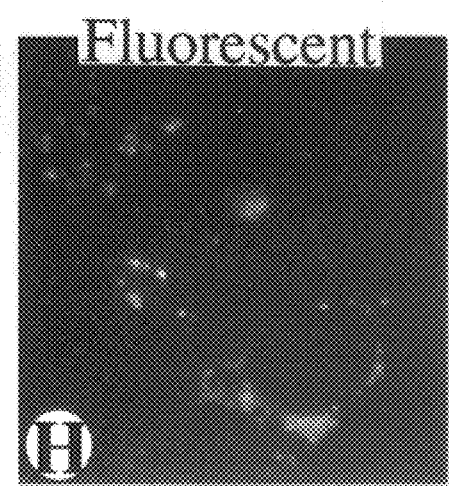

Annexin V binding to injured neurons is reversible and reproducible. By employing the reversible annexin V methods of the present invention, the time when cultured neurons externalized phosphatidylserine at the plasma membrane was determined. FIGS. 1A–1H illustrate the reversibility of the annexin V and phosphatidylserine interaction following removal of calcium. The figures are a series of images of the same microscope field. FIGS. 1A, 1C, 1E and 1G are generated using the transmitted light illustrating the neurons. The corresponding FIGS. 1B, 1D, 1F and 1H were obtained using 490 nm excitation and 585 nm emission wavelengths to locate the PE label on the surface of neurons undergoing PCD. Five hours following exposure to SNP (300 $\mu$M), the neurons were examined prior to the addition of the label to demonstrate that there was no background fluorescence (FIG. 1B). In FIGS. 1C and 1D, the neurons were stained with annexin V-phycoerythrin conjugate. Stained, fluorescent neurons, undergoing PCD, are indicated in FIG. 1D. The label was then removed by washing three times in calcium-free buffer. The efficiency of removal is demonstrated while the neurons were still present (FIGS. 1E and 1F). Neurons could then be re-stained and imaged (FIGS. 1G and 1H).

Figure 2:
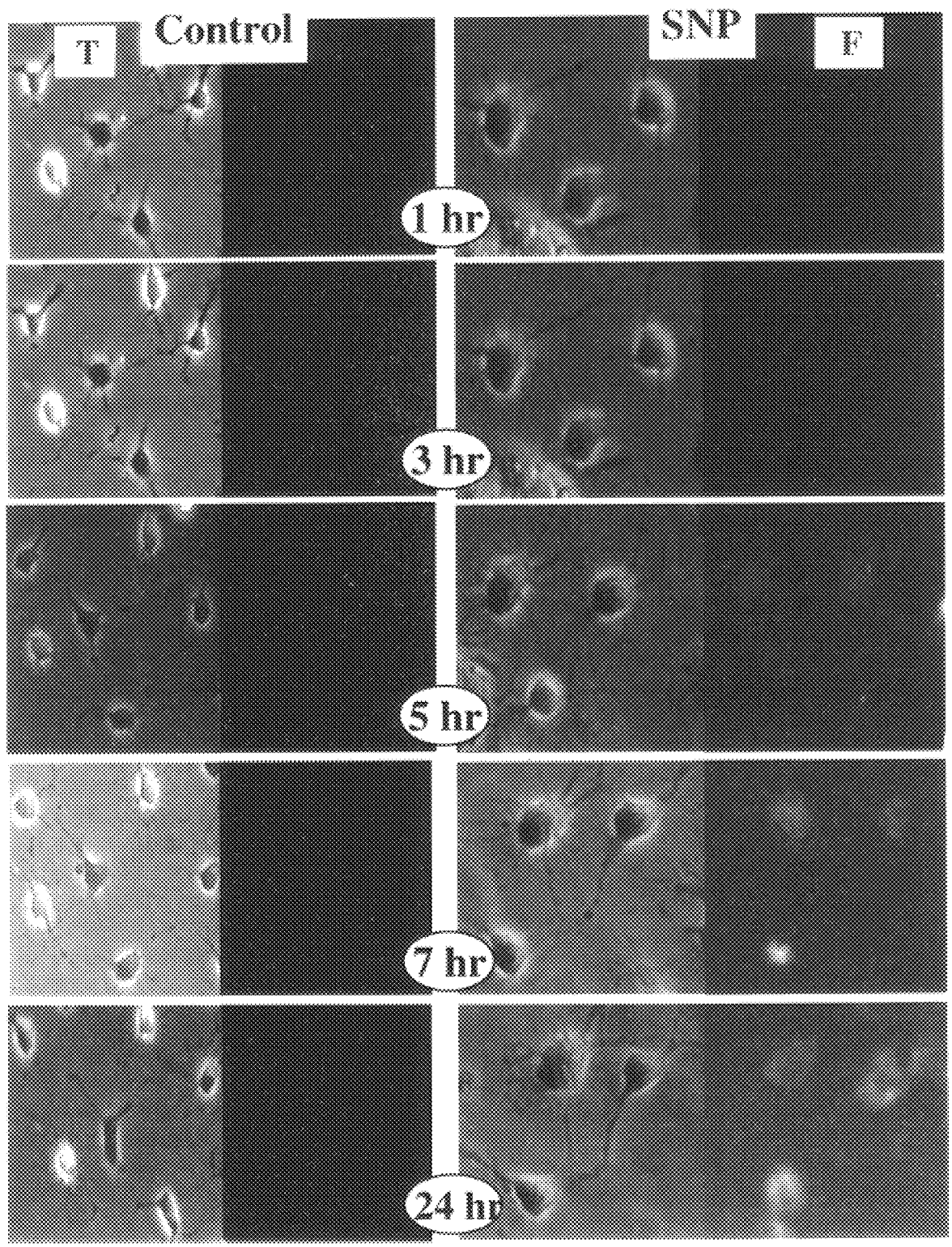
FIG. 2 is a series of photomicrographs showing the tracking of individual neurons over time, illustrating a progressive increase in annexin V labeling following free radical injury.
Figure 3:
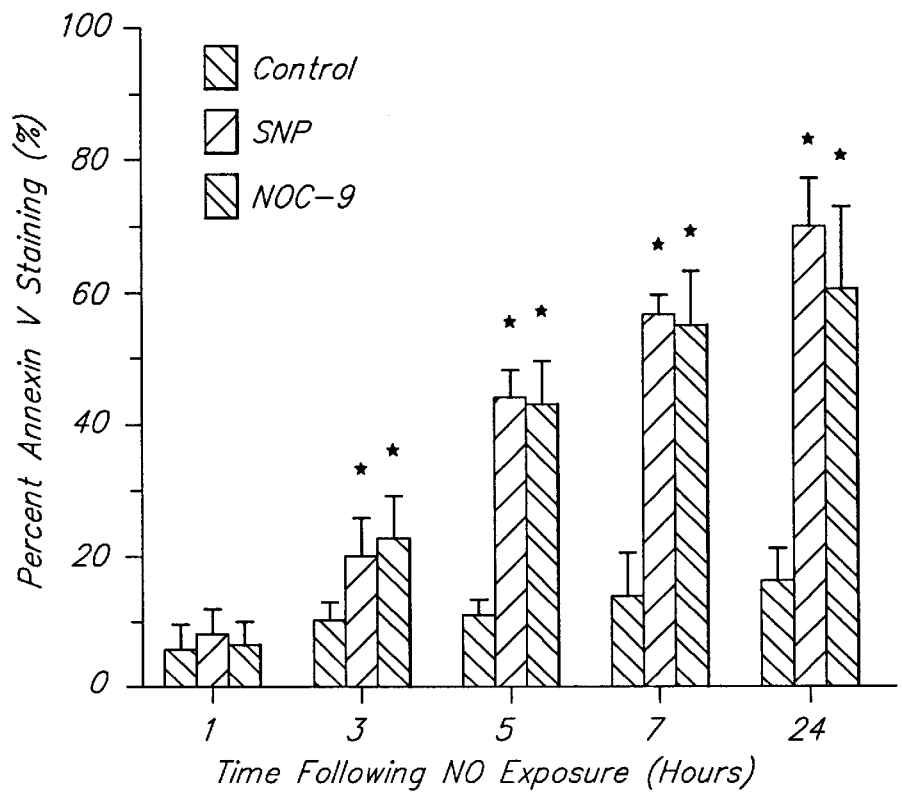
FIG. 3 is a bar graph showing the percent annexin V staining increase over time, following NO exposure.

NO exposure induces a progressive increase in phosphatidylserine residue translocation. FIG. 2 illustrates a series of representative images obtained to characterize changes in annexin V labeling over a 24 hour period. Representative fields of stained neurons are shown indicating minimal induction of PCD in control cultures (left column, T=transmitted light, F=fluorescence) and induction of PCD in cultures exposed to SNP (300 $\mu$M) (right column, T=transmitted light, F=fluorescence). Over a 24 hour course, a statistically insignificant induction in annexin V labelling of control cultures may be secondary to repeated mechanical manipulation. The degree of annexin V staining was further assessed by determining the proportion of labelled neurons in each microscope field. Initial percent annexin V staining in untreated control cultures at the 1 hour time period was 6+4% (FIG. 3). This amount of annexin V staining approached a trend to gradually increase in the same neuronal cells to 17±4%, but was not statistically significant (FIG. 3). In FIG. 3, data represents the mean and standard error from seven individual experimental cultures. In each experiment, the percentage of stained neurons was counted in 3–7 discrete fields with 5–25 neurons in each field. Results of neuronal cultures exposed to NO (*) were significantly different from control (untreated) cultures not exposed to NO, p<0.05 by ANOVA.

In neurons exposed to NO, a progressive and significant increase in annexin V labeling was evident over a 24 hour period. FIG. 2 illustrates a representative set of images for the NO generator SNP (300 $\mu$M). Within 3 hours following the exposure to NO, annexin V labelling is significantly increased from approximately 5% to 20% in the identical neuronal cells (FIGS. 2 and 3), suggesting a rapid induction of PCD. These neurons continue to significantly progress with phosphatidylserine membrane translocation to a maximum of approximately 60% over a 24 hour time period (FIGS. 2 and 3). Thus, the ability to follow the temporal course of phosphatidylserine membrane translocation in individual neurons following free radical exposure with NO demonstrates that the resultant induction of PCD is both an early (within 3 hours) and a robust process that serially progresses in individual neurons over a 24 hour course.

Figure 4:
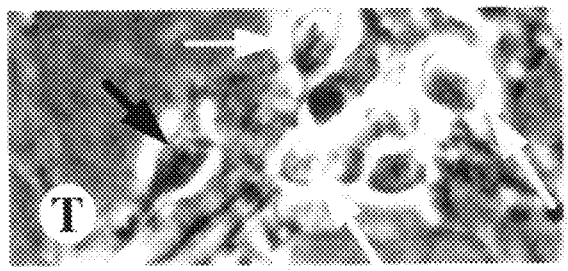
FIG. 4 is a series of photomicrographs showing the same field of neurons five hours following NOC-9 exposure, illustrating that phosphatidylserine exposure precedes loss of membrane integrity.
Figure 4:
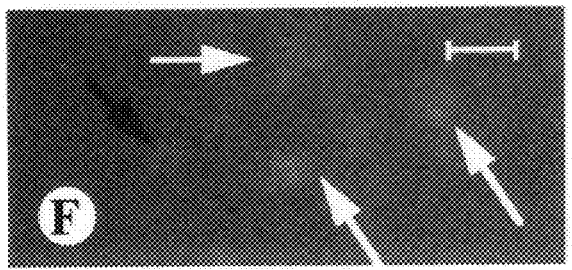

Annexin V binding identifies neurons early in PCD prior to the loss of membrane integrity. Translocation of membrane phosphatidylserine residues has been reported to be an early marker of PCD induction. Rimon, G. et al., *J. Neurosci Res.* 48:563–570 (1997). If this is the case, then positive labelling of externalized phosphatidylserine residues should occur prior to the onset of cellular membrane disruption. The ability of annexin V to identify early PCD induction prior to the onset of cellular membrane induction was thus characterized with a dye exclusion system. In this set of experiments, the ability of neurons labelled with annexin V to simultaneously stain with trypan blue was assessed. Following the identification of neurons that label for annexin V at each time period, warmed (37° C.) 0.4% trypan blue was added in a 1:1 volume:volume dilution for one minute, removed, and then neurons were re-imaged. At the time periods of 3 hours, 5 hours, and 7 hours, the majority of neurons labelling positive for annexin V did not stain for trypan blue. FIG. 4 (A and B) is a representative image at the 5 hour time period. In FIG. 4, the left panel (T) illustrates the transmitted light image following addition of trypan blue dye, the black arrow identifies a neuron unable to exclude trypan blue and in the corresponding fluorescent image (F), the annexin V labeled neurons are indicated with white arrows and the neuron unable to exclude trypan blue is identified by the black arrow. FIG. 4 illustrates that annexin V labelling of phosphatidylserine residue translocation precedes cellular membrane disruption that is detected with trypan blue staining. In contrast, over a 24 hour period, labelling with annexin V coincides with trypan blue staining in the same neuronal population, suggesting that PCD has progressed to a level that now involves cellular membrane disruption. These results correlate with prior studies that demonstrate PCD expression and trypan blue staining in 70% of primary hippocampal neurons 24 hours post NO exposure. Maiese, K. et al., *J. Cereb. Blood Flow Metab.* 15:440449 (1995); Maiese, K. et al., *J. Neurosci.* 13:3034–3040(1993); Vincent, A. M. et al., *J. Neurosci Res.* 50:549–564(1997). Thus, the method is sensitive for the assessment of the initial stages of PCD induction prior to more "global" cellular injury.

Figure 5:
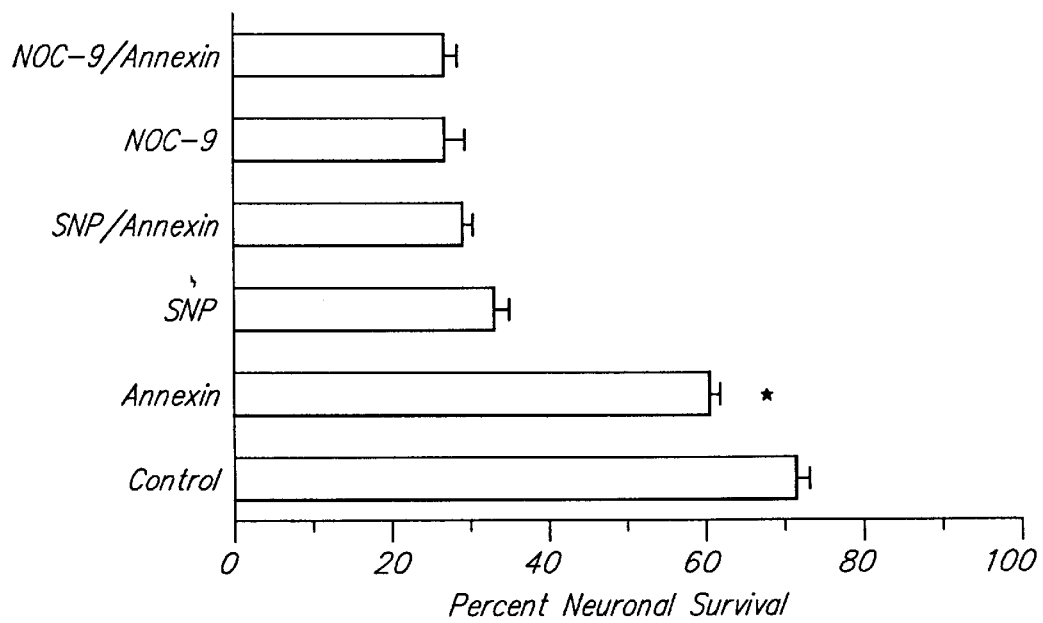
FIG. 5 is a bar graph showing the percent neuronal survival under various circumstances, illustrating that repeated staining with annexin V does not alter neuronal survival.

Annexin V staining does not independently alter neuronal survival Depending on the mode and concentration of application, annexin V application can have either toxic or neurotrophic effects on neurons. Takei, N. et al., *Neurosci Lett.* 171:59–62 (1994). Neurotrophic effects have been reported with a continuous 5 day exposure within a low concentration range (1–30 ng/ml). Although a brief application of annexin V for 10 minutes is employed, the concentration of annexin V (3 ug/ml) is greater than concentrations that have been demonstrated to yield neurotrophic effects. For these reasons, the ability of annexin V to alter neuronal survival in primary hippocampal cultures was investigated. Assessing neuronal survival over a 24 hour period, repeated application of annexin V at 1 hour, 3 hours, 5 hours, 7 hours, and 24 hours slightly decreased neuronal survival from 72±2% (untreated control) to 61±2% (repeated annexin application) (FIG. 5, data represents the mean and standard error from two separate experimental cultures). Yet, application of annexin V in conjunction with a NO generator did not significantly alter neuronal survival when compared to application of a NO generator alone. In light of these results, annexin V application appears not to be directly toxic to the neurons, but a 10% decrease in neuronal survival may be secondary to cellular mechanical disruption following repeated washing and staining applications over a 24 hour period.

Figure 6A:
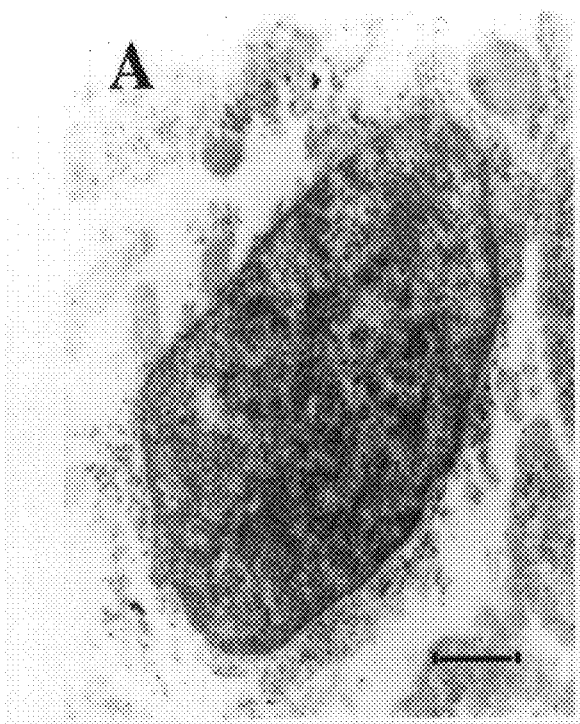
FIGS. 6A–6D are a series of photomicrographs of a neuronal nucleus at various times following exposure to NOC-9, illustrating that nuclear morphological changes correlate with annexin labeling.
Figure 6B:
Figure 6C:
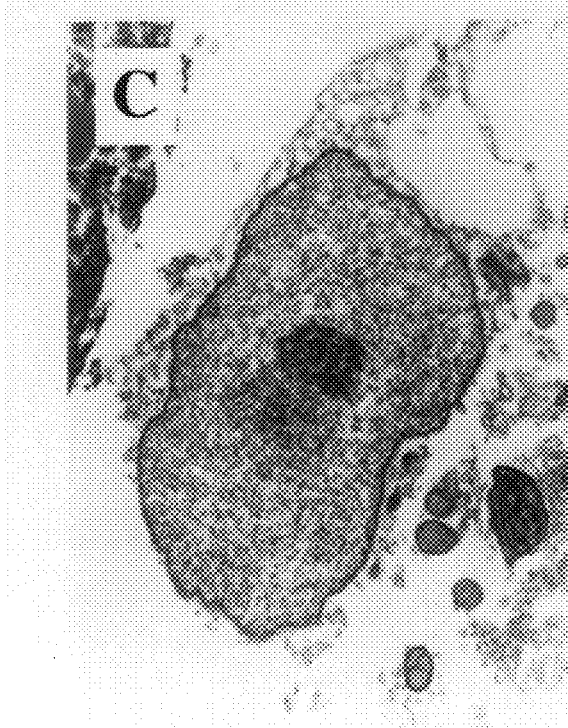
Figure 6D:
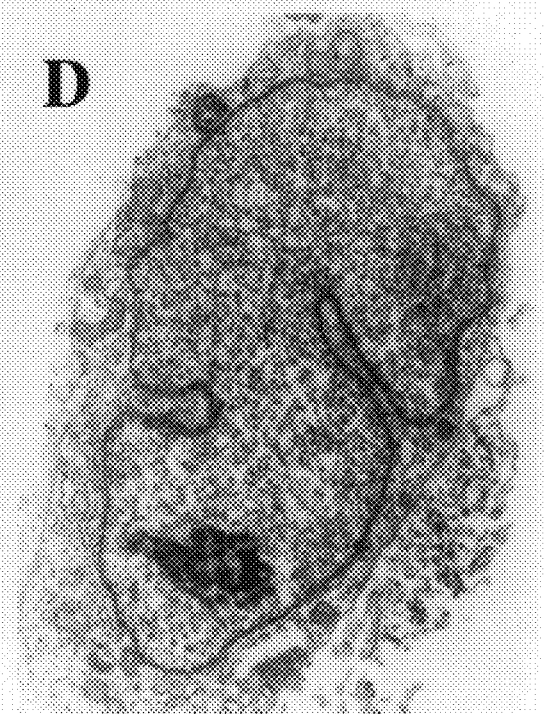

Annexin V staining correlates closely with changes in nuclear morphology. The results illustrate that the methods of the present invention provide a sensitive approach for the early detection of the induction of PCD. Yet, it also is vital to assess the specificity of the method to detect PCD. Electron microscopy provides a secondary analysis to visualize changes in the neuronal subcellular structure that are consistent with PCD. As shown in FIGS. 6A–6D, primary hippocampal neurons were exposed to a NO generator and then processed 1 hour (A), 3 hours (B), 5 hours (C), 7 hours (D), and 24 hours later for transmission electron microscopy. Evidence for apoptotic neuronal cell death was characterized by the preservation of membrane integrity and internal organelle structure, and by the presence of chromatin condensation with nuclear fragmentation (FIGS. 6A–6D). Assessment by electron microscopy for PCD closely paralleled PCD characterization through the annexin V labelling. Approximately 10% or fewer neurons displayed evidence of PCD after 1 hour, with the majority of neurons showing no evidence of PCD (FIG. 6A). A slightly greater proportion (10–20%) of neurons displayed some chromatin condensation after 3 hours (FIG. 6B). At 5 hours, approximately 35% of the neurons were identified with chromatin condensation (FIG. 6C). The percentage of neurons on electron microscopy that were consistent with PCD increased to approximately 50% by 7 hours (FIG. 6D) and to almost 70% by 24 hours (data not shown).

The methods described herein for identifying the initial induction of PCD and following the course of PCD progression are specific, sensitive, and non-toxic. Within one to three hours following a free radical insult with a NO generator, the onset of phosphatidylserine residue membrane translocation is identified. This exposure of the phosphatidylserine residues was consistent with the induction of PCD and was independent of global cellular injury as detected with the trypan blue dye exclusion method. The use of an exclusion dye is an important characterization the methods of the present invention to ensure that annexin V staining is facilitated through loss of membrane asymmetry and not through loss of membrane integrity. Co-assessment of phosphatidylserine labelling with electron microscopy imaging further supported the specificity and sensitivity of the methods. Appearance of the nuclear morphological alterations documented by electron microscopy paralleled the ability to identify phosphatidylserine residue membrane translocation. The results are consistent with prior studies that demonstrate a close correlation between chromatin condensation identified by flow cytometry and annexin V labelling. Koopman, G. et al., *Blood* 84:1415–1420 (1994). This simultaneous appearance of chromatin condensation and phosphatidylserine exposure also suggests that these cellular processes may be down-stream of other signal transduction events that initiated PCD.

In summary, the methods of the present invention provide for the critical assessment of both the onset of PCD and the subsequent progression of PCD. The methods may be used by those skilled in the art to identify the initial stages of PCD and to follow the course of PCD in individual living cells. Staining with fluorescent annexin V for microscopic examination is rapid, reliable, and reversible, permitting minimal disruption to the cells under examination.

The foregoing discussion discloses and describes merely exemplary embodiments of the present invention. One skilled in the art will readily recognize from such discussion, and from the accompanying drawings and claims, that various changes, modifications and variations can be made therein without departing from the spirit and scope of the invention as defined in the following claims.

Patent and literature references cited herein are incorporated by reference as if fully set forth.

We claim:

1. A method for detecting the presence of phosphatidylserine residues on the surface of a viable cell over a period of time, comprising:
    a) maintaining a viable cell on a slide;
    b) staining the cell with annexin V;
    c) visualizing the cell of step b) to detect the presence of phosphatidylserine residues on the cell surface;
    d) washing the cell to remove the annexin V;
    e) staining the cell of step d) with annexin V; and
    f) visualizing the cell of step e) to detect the presence of phosphatidylserine residues on the cell surface.

2. The method of claim 1, wherein the cell is selected from the group consisting of neuronal cells, fibroblasts, epithelial cells, stromal cells and thymocytes.

3. The method of claim 1, wherein the visualizing of the cell is by microscopy.

4. The method of claim 1, wherein in step d) the cell is washed with a calcium-free dissociation buffer.

5. A method for detecting the presence of phosphatidylserine residues on the surface of a viable cell over a period of time, comprising:
    a) maintaining a viable cell on a slide;
    b) staining the cell with annexin V;
    c) visualizing the cell of step b) to detect the presence of phosphatidylserine residues on the cell surface;
    d) washing the cell to remove the annexin V;
    e) contacting the cell of step d) with an agent;
    f) staining the cell of step e) with annexin V; and
    g) visualizing the cell of step f) to detect the presence of phosphatidylserine residues on the cell surface.

6. The method of claim 5, wherein the cell is selected from the group consisting of neuronal cells, fibroblasts, epithelial cells, stromal cells and thymocytes.

7. The method of claim 5, wherein the visualizing of the cell is by microscopy.

8. The method of claim 5, wherein in step d) the cell is washed with a calcium-free dissociation buffer.

9. The method of claim 5, wherein the agent is a therapeutic agent.

10. The method of claim 5, wherein the agent is a toxic agent.

11. A method for detecting the presence of phosphatidylserine residues on the surface of a viable cell over a period of time, comprising:

a) maintaining a viable cell on a slide;

b) contacting the cell of step a) with a programmed cell death-causing agent;

c) staining the cell of step b) with annexin V;

d) visualizing the cell of step c) to detect the presence of phosphatidylserine residues on the cell surface;

e) washing the cell of step d) to remove the annexin V;

f) contacting the cell of step e) with a therapeutic agent;

g) staining the cell of step f) with annexin V; and h) visualizing the cell of step g) to detect the presence of phosphatidylserine residues on the cell surface.

12. The method of claim 11, wherein the cell is selected from the group consisting of neuronal cells, fibroblasts, epithelial cells, stromal cells and thymocytes.

13. The method of claim 11, wherein the visualizing of the cell is by microscopy.

14. The method of claim 11, wherein in step e) the cell is washed with a calcium-free dissociation buffer.

15. The method of claim 11, wherein the programmed cell death-causing agent is NO.

* * * * *